United States Patent [19]

Maeyama et al.

[11] Patent Number: 4,618,488

[45] Date of Patent: Oct. 21, 1986

[54] TOOTHPASTE COMPOSITION

[75] Inventors: Tsutomu Maeyama, Chiba; Shigeru Ishii; Kenji Kaneko, both of Tokyo, all of Japan

[73] Assignee: Lion Corporation, Tokyo, Japan

[21] Appl. No.: 759,360

[22] Filed: Jul. 26, 1985

[30] Foreign Application Priority Data

Jul. 31, 1984 [JP] Japan ................................ 59-162661
Sep. 7, 1984 [JP] Japan ................................ 59-187424

[51] Int. Cl.$^4$ ............................................. A61K 7/16
[52] U.S. Cl. ..................................................... 424/49
[58] Field of Search ..................................... 424/49-58

[56] References Cited

U.S. PATENT DOCUMENTS

| | | | |
|---|---|---|---|
| 3,939,262 | 2/1976 | Kim | 424/49 |
| 4,244,707 | 1/1981 | Wason | 424/52 |
| 4,312,845 | 1/1982 | Wason | 424/52 |

FOREIGN PATENT DOCUMENTS 2038303 7/1980 United Kingdom .

Primary Examiner—Shep K. Rose
Attorney, Agent, or Firm—Birch, Stewart, Kolasch & Birch

[57] ABSTRACT

A stable toothpaste composition which includes as an abrasive amorphous silica or silicate having a specific surface area of 5 to 100 m$^2$/g as measured by BET method with nitrogen adsorption and a specific surface area of 100 to 400 m$^2$/g as measured by BET method with water vapor adsorption.

24 Claims, No Drawings

TOOTHPASTE COMPOSITION

BACKGROUND OF THE INVENTION

1. Field of the Invention

The present invention relates to a toothpaste composition which is superior in time-dependent stability, and more particularly, it relates to a toothpaste composition which remains transparent for a long storage time

2. Description of the Prior Art

Heretofore, a variety of silica and silicate abrasives have been proposed as the abrasive for transparent toothpaste. The conventional silica or silicate abrasive, however, has some disadvantages. That is, it is poor in time-dependent stability. Where it is used for transparent toothpaste by mixing it with a transparent vehicle having substantially the same refractive index as it, it changes in refractive index in the toothpaste after a long period of storage. As a result, the toothpaste becomes poor in transparency because there occurs a discrepancy between the refractive index of silica or silicate abrasive and that of the transparent vehicle.

The conventional silica and silicate abrasives are of high refraction type having a refractive index of about 1.46. Where toothpaste is prepared with such a silica or silicate abrasive, it is necessary to prepare a transparent vehicle having approximately the same high refractive index. This is accomplished only by reducing the amount of water in the transparent vehicle and by increasing the amount of glycerin and sorbitol which have a high refractive index. However, increasing the amount of glycerin and sorbitol raises the production cost of transparent toothpaste. In addition, a large amount of glycerin and sorbitol excessively sweetens the toothpaste that contains them, and the toothpaste containing a large amount of glycerin gives a hot feeling to the mouth due to the heat of solution of glycerin. Furthermore, the toothpaste incorporated with a large amount of glycerin and sorbitol tends to rope when extruded from a tube.

SUMMARY OF THE INVENTION

An object of the present invention is to provide a toothpaste composition which is superior in time-dependent stability.

Another object of the present invention is to provide a transparent toothpaste composition which remains transparent for a long storage time.

In order to attain the above objects, the present inventors investigated the abrasive which is superior in time-dependent stability in toothpaste and keeps the toothpaste containing it transparent for a long period of time. As a result, it was found that amorphous silica or silicate as specified below is stable in a toothpaste composition, maintaining its refractive index, and is superior in time-dependent stability. The amorphous silica or silicate has a specific surface area of 5 to 100 $m^2/g$ as measured by the BET adsorption method with nitrogen (referred to as "specific surface area measured by nitrogen adsorption" hereinafter) and a specific surface area of 100 to 400 $m^2/g$ as measured by the BET adsorption method with water vapor (referred to as "specific surface area measured by water vapor adsorption" hereinafter).

Heretofore, a variety of silica and silicate abrasives which differ in specific surface area (measured by nitrogen adsorption) have been used for the preparation of transparent toothpaste. As a result of their investigation, the present inventors found that the conventional silica or silicate abrasive has the specific surface area measured by nitrogen adsorption which is approximately equal to that measured by water vapor adsorption. The ratio of the latter to the former is 0.5 to 2.0. This conventional type of silica or silicate abrasive is poor in time-dependent stability as mentioned above and its refractive index changes with time when it stays in toothpaste. The present inventors also found that amorphous silica or silicate having a specific surface area in a certain range, i.e the amorphous silica or silicate having a specific surface area of 5 to 100 $m^2/g$ as measured by nitrogen adsorption and a specific surface area of 100 to 400 $m^2/g$ as measured by water vapor adsorption, and preferably the ratio of the specified surface area as measured by the BET method with water vapor adsorption to the specific surface area as measured by the BET method with nitrogen being 2 to 30, is superior in time-dependent stability and its refractive index remains almost unchanged when toothpaste containing it is stored for a long period of time. It was further found that better results are obtained where the silica or silicate has a pore volume of 0.10 to 0.15 ml/g as measured by nitrogen adsorption and has a pore volume of 0.2 to 0.7 ml/g as measured by water vapor adsorption. In addition, this kind of silica or silicate can be made to have a low refractive index of about 1.420 to 1.450. Where low refraction silica or silicate like this is used as an abrasive of transparent toothpaste, it is possible to lower the content of glycerin and sorbitol which have a high refractive index and to increase the content of water. This solves problems such as high production cost and the undesirable feeling during use which are caused by adding a large amount of glycerin and sorbitol. Such silica or silicate keeps its refractive index even when the toothpaste containing it is stored for a long time. Therefore, the toothpaste incorporated with it remains transparent and gives good feeling during use, and can be produced at a low cost. The present invention is based on these findings.

Therefore, the present invention provides a toothpaste composition comprising as an abrasive amorphous silica and/or silicate having a specific surface area of 5 to 100 $m^2/g$ as measured by BET method with nitrogen adsorption and a specific surface area of 100 to 400 $m^2/g$ as measured by BET method with water vapor adsorption.

The above and other objects, features and advantages of the present invention will be more fully understood from the following description.

DETAILED DESCRIPTION OF THE INVENTION

The toothpaste composition of this invention contains as an abrasive amorphous silica or silicate having a specific surface area of 5 to 100 $m^2/g$ as measured by nitrogen adsorption and a specific surface area of 100 to 400 $m^2/g$ as measured by water vapor adsorption. The toothpaste composition containing this type of silica or silicate is superior in time-dependent stability and keeps its quality even after storage for a long period of time. The amorphous silica or silicate can be produced in various ways. Hydrated synthetic silica or silicate is preferable, and one having the above-mentioned specific surface area is particularly superior in time-dependent stability.

The silica or silicate used in this invention has a specific surface area as specified above. The preferred one has a specific surface area of 5 to 50 m$^2$/g as measured by nitrogen adsorption and a specific surface area of 150 to 300 m$^2$/g as measured by water vapor adsorption. The ratio of the specified surface area as measured by the BET method with water vapor adsorption to the specific surface area as measured by the BET method with nitrogen may preferably be 2 to 30, and more preferably 3 to 20. Moreover, the preferred one has a pore volume of 0.01 to 0.15 ml/g, particularly 0.02 to 0.1 ml/g, as measured by nitrogen adsorption and a pore volume of 0.2 to 0.7 ml/g, particularly 0.3 to 0.6 ml/g, as measured by water vapor adsorption.

The preferred silica or silicate used in this invention should have a specific surface area as measured by nitrogen adsorption, a specific surface area as measured by water vapor adsorption, and a ratio of the two values, as specified above. In addition, it should preferably have a specific surface area of 5 to 60 m$^2$/g as measured by CTAB method. The more preferred anhydrous silica or silicate should have a specific surface area of 5 to 60 m$^2$/g, preferably 10 to 50 m$^2$/g, as measured by BET method with nitrogen adsorption and a specific surface area of 5 to 60 m$^2$/g, preferably 10 to 40 m$^2$/g as measured by CTAB method, with the difference between the two values being lower than 40 m$^2$/g, preferably lower than 30 m$^2$/g. The amorphous silica or silicate as specified above is superior in timedependent stability, maintains its refractive index, and provides a proper degree of abrasiveness. The anhydrous silica or silicate used in this invention denotes silica or silicate which has been crushed and dried at 105° C. for about 2 hours until a constant weight is reached.

The silica or silicate to be suitably used in this invention is one which has a liquid absorption of 0.4 to 2.0 ml/g, particularly 0.6 to 1.5 ml/g, and has a specific gravity of 0.9 to 2.3.

The silica or silicate used in this invention should preferably have a refractive index of 1.420 to 1.450, particularly 1.430 to 1.445, where it is incorporated into transparent toothpaste. Using low refraction silica or silicate permits a reduction in the content of glycerin and sorbitol in order to lower the refractive index of the transparent vehicle. The silica or silicate can have such a low refractive index of 1.420 to 1.450 when it has the specific surface areas as measured by nitrogen adsorption and water vapor adsorption as specified above. Thus, silica or silicate with a desired low refractive index can be produced by properly regulating the specific surface area.

The preferred amorphous silica or silicate used in this invention is one which contains more than 70%, preferably more than 85% by weight of SiO$_2$. The silicate may be so-called aluminosilicate or zirconosilicate in which SiO$_2$ is combined with aluminum or zirconium. In this case, the content of aluminum or zirconium should preferably be less than 10%, preferably less than 2% by weight based on the weight of SiO$_2$. Moreover, the silica or silicate used in this invention may contain sodium, potassium, lithium, calcium, magnesium, hafnium, etc. which usually enter during the production of silica or silicate. Such metal components may be combined with SiO$_2$ or dispersed in silica or silicate, and their amount may be less than 10%, preferably less than 5% by weight based on the weight of SiO$_2$. The water content in silica or silicate should preferably be less than 20%, more preferably less than 15% by weight at 25° C. and 70% RH, and the loss on ignition should preferably be less than 15%, more preferably less than 10%.

According to this invention, the abovementioned amorphous silica or silicate is used as an abrasive. The average particle diameter of the silica or silicate as measured by SEM method should preferably be 0.01 to 1 μm, particularly 0.05 to 0.5 μm, and the average particle diameter as measured by sedimentation method should preferably be 1 to 30 μm, particularly 1 to 15 μm. The abrasiveness of the silica or silicate should preferably be 1 to 50 mg, particularly 1 to 20 mg as measured by the copper plate abrasion method. The silica or silicate used in this invention can be made to have a proper degree of abrasiveness by selecting a proper specific surface area as measured by nitrogen adsorption. As the specific surface area as measured by nitrogen adsorption becomes greater, the abrasiveness may tend to become lower.

The amorphous silica or silicate is incorporated into a toothpaste composition in varied amounts according to the intended use. The amount is usually 1 to 50%, particularly 5 to 35% by weight in the total weight of the composition.

The silica or silicate used in this invention can be produced by reacting a solution of alkali metal silicate with hydrochloric acid or sulfuric acid in the presence of an electrolyte. The production process may include the reaction step in which the reaction system is adjusted to pH 10.0 and silica is formed, and the neutralization step in which the reaction system is adjusted to pH 8.0 to 6.5. The rate of adding chlorine ions or sulfate ions in the neutralization step and the rate of adding chlorine ions or sulfate ions in the silica forming step may be established so that their ratio is at least 5:3. The neutralization step may be finished within 30 minutes, and aging may be performed for at least 10 minutes.

The production process mentioned above will be described in more detail. The alkali metal silicate includes sodium, potassium, or lithium silicate. Sodium silicate is most common because of its comparative low price. Those alkali metal silicates having a molar ratio (SiO$_2$/X$_2$O, where X is an alkali metal) of 2 to 4 can be used. Hydrochloric acid or sulfuric acid can be used to acidify the alkali metal silicate. The concentration of the acid may be 5 to 15% by weight, and the concentration of the alkali metal silicate solution may be 5 to 15% by weight (as SiO$_2$). These concentrations are adequate to impart the desired properties to silica if other conditions are properly selected.

The electrolyte should preferably be an alkali metal salt of mineral acid, such as sodium or potassium salt of mineral acid. Examples of such salts include sodium chloride, potassium chloride, sodium sulfate, potassium sulfate, sodium carbonate, potassium carbonate, sodium nitrate, and potassium nitrate. These salts are used in an amount of 10 to 60% by weight based on the amount of SiO$_2$. The amount should be properly selected in relation to the abrasiveness of the silica.

The above-mentioned process for producing the silica or silicate used in this invention is initiated by reacting a solution of alkali metal silicate with hydrochloric acid or sulfuric acid in the presence of an electrolyte. The electrolyte may previously be added to the solution of alkali metal silicate. This is desirable to impart a proper degree of abrasiveness to silica or silicate. Alternatively, the electrolyte may be added to hydrochloric acid or sulfuric acid if the amount of the electrolyte, the reaction temperature, and the reaction time are properly selected. In the normal mode of reaction where an electrolyte is previously added to a solution of alkali metal silicate, a solution of alkali metal silicate which may vary in concentration and composition and a solution of electrolyte may be added together or separately to a proper reaction vessel, or alternatively, a solution of alkali metal silicate to which an electrolyte has previously been added may be added to a reaction vessel. The reaction may preferably be carried out with sufficient agitation, and the reaction temperature may preferably be kept at 0 to 100° C.

The process for producing the silica or silicate used in this invention comprises two steps: silica forming step in which the reaction system is adjusted to pH 10.0, and neutralization step which terminates the reaction at pH 8.0 to 6.5. The rate of adding chlorine ions or sulfate ions in the neutralization step and the rate of adding chlorine ions or sulfate ions in the silica forming step may be established so that their ratio is at least 5:3. The neutralization step may be finished within 30 minutes, and aging may be performed for at least 10 minutes.

In the silica forming step, more than 95% of silica ($SiO_2$) component in the alkali metal silicate solution separates out. This step should preferably be performed by adding hydrochloric acid or sulfuric acid over a period of 40 minutes to 4 hours. The period should preferably be properly selected according to the amount of electrolyte and the reaction temperature. A period of 1 to 2 hours is preferable for efficient industrial operation.

In the neutralization step hydrochloric acid or sulfuric acid is added so that the pH of the reaction system is lowered from pH 10.0 to pH 8.0–6.5 after most silica has separated out. This neutralization step is not so important where the resulting silica is not required to have high abrasiveness. But for the production of highly abrasive silica, the neutralization step may not be excessively long and the aging step may not be excessively short. Otherwise, it may be difficult to produce silica which is superior in transparency and time-dependent stability. The reason for this is not known well. The neutralization step should preferably be finished within 30 minutes. The rate of adding chlorine ions or sulfate ions in the neutralization step and the rate of adding chlorine ions or sulfate ions in the silica forming step should preferably be established so that their ratio is at least 5:3. The aging step should preferably be performed for at least 10 minutes. In other words, the neutralization step should preferably be finished within a short time and the aging step should preferably be performed for at least 10 minutes. This greatly improves the physical properties of silica, stabilizes the quality of silica, and increases the productivity of silica.

The reaction system is adjusted to pH 8.0 - 6.5 in the neutralization step. This establishes a uniform refractive index of 1.42 to 1.45 (measured in the glycerin-water system), which is desirable for silica to be added to transparent toothpaste. If the reaction system has a pH of 6.5 or below, the resulting silica fluctuates in refractive index and is not suitable for transparent toothpaste. Conversely, if the reaction system has a pH of 8.0 or above at the end of reaction, the resulting silica results in a turbid toothpaste and has a high pH which makes it unsuitable for toothpaste.

In the production of silica or silicate, it is possible to add aluminum sulfate, aluminum chloride, calcium chloride, magnesium chloride, or basic salt thereof; or sodium fluoride, potassium fluoride, or ammonium fluoride to the alkali metal silicate solution or hydrochloric acid or sulfuric acid previously or at the time of reaction in order to adjust abrasiveness and refractive index.

After the neutralization step, silica is filtered off, washed with water, dried, and crushed in the usual way.

The process for producing the silica or silicate used in this invention is not limited to the above-mentioned one; but other processes may be used.

The toothpaste composition of this invention may be incorporated, if necessary, in addition to the above-mentioned amorphous silica or silicate, with other abrasives such as calcium secondary phosphate, calcium carbonate, calcium pyrophosphate, insoluble sodium metaphosphate, other silica abrasives, aluminum oxide, aluminum hydroxide, titanium dioxide, and resin. The amount of these additional abrasive may preferably be less than 20%, particularly less than 10% by weight in the total weight of the composition so that the silica or silicate of this invention exhibits its performance. In the case of transparent toothpaste, these additional abrasives should be less than 20%, particularly less than 10% by weight of the weight of the silica or silicate of this invention. In the meantime, the transparent toothpaste embraces both completely transparent ones and translucent ones.

The toothpaste composition of this invention can be produced by mixing the above-mentioned abrasive and the toothpaste vehicle. The toothpaste vehicle is composed of water and commonly used components such as binder (e.g., sodium carboxymethylcellulose, hydroxyethylcellulose, alginate, carrageenan, gum arabic, and polyvinyl alcohol), humectant (e.g., polyethylene glycol, sorbitol, glycerin, and propylene glycol), surface active agent (e.g., sodium lauryl sulfate, sodium dodecylbenzenesulfonate, sodium hydrogenated coconut fatty acid monoglyceride monosulfate, sodium laurylsulfoacetate, sodium N-lauroylsarcosinate, N-acylglutamate, lauroyl diethanolamide, and sucrose fatty acid ester), flavor (e.g., peppermint oil, spearmint oil, l-menthol, carvone, eugenol, and anethole), sweetener (e.g., sodium saccharin, stevioside, neohesperidyldihydrochalcone, glycyrrhizin, perillartine, and p-methoxycinnamic aldehyde), coloring matter, preservative, and effective ingredients (e.g., dextranase, mutanase, sorbic acid, alexidine, $\beta$-glycyrrhetinic acid, hinokitiol, chlorhexidines, alkylglycine, alkyldiaminoethylglycine salt, allantoin, $\epsilon$-aminocaproic acid, tranexamic acid, azulene, vitamin E, water-soluble primary or secondary phosphate, quaternary ammonium compound including cetylpyridinium chloride, sodium chloride, crude drug extract, sodium monofluorophosphate, sodium fluoride, and stannous fluoride). In the meantime, the silica or silicate of this invention hardly absorbs fluorides, permitting fluorides in the toothpaste composition to be stably preserved. Thus fluorides can be effectively incorporated into the toothpaste composition.

The blending amount of binder is preferably in the range of 0–5%, particularly 0.1–5% by weight of the toothpaste composition. The blending amount of humectant is preferably in the range of 10–80%, particularly 30–60% by weight of the composition. The blending amount of surface active agent is preferably in the range of 0.1–5%, particularly 0.5–2% of the composition. The blending amount of sweetener is preferably 0.01–5%, particularly 0.05–2% by weight of the composition. The blending amount of flavor is preferably in the range of 0.1–5%, particularly 0.5–2% by weight of the composition.

Transparent toothpaste can be produced only when the above-mentioned transparent toothpaste vehicle has substantially the same refractive index as the silica or silicate of this invention. Where the silica or silicate has a low refractive index of 1.420 to 1.450, the transparent toothpaste vehicle should also have a low refractive index accordingly. This means that it is possible to reduce the content of glycerin and sorbitol which have a high refractive index and to increase the content of water instead. The reduction of glycerin and sorbitol eliminates the ropiness of toothpaste which is encountered when toothpastes is extruded from a tube, and also improves the feeling during use. In addition, the increase of water content leads to the reduction of production cost.

The toothpaste produced according to this invention should preferably have pH 5-9.

The toothpaste composition of this invention is characterized by that it contains as an abrasive amorphous silica or silicate which has a specific surface area of 5 to 100 m$^2$/g as measured by BET method with nitrogen adsorption and a specific surface area of 100 to 400 m$^2$/g as measured by BET method with water vapor adsorption. It is superior in time-dependent stability and it permits the transparent toothpaste composition containing it to remain transparent for a long period of time.

The invention is described in more detail with reference to the following examples, although the invention is not limited to the examples.

EXAMPLES 1 and 2 and COMPARATIVE EXAMPLES 1 and 2

Several kinds of transparent toothpaste in which synthetic amorphous precipitated silica having the properties shown in Tables 1 and 2 is used as an abrasive were prepared according to the formulation shown in Table 3.

TABLE 1

| Silica | Nitrogen Adsorption (Liquid Nitrogen Temperature) | | Water Vapor Adsorption (25° C.) | |
|---|---|---|---|---|
| | Specific Surface Area (BET method) | Pore Volume (P/Po = 0.976*[1]) | Specific Surface Area (BET method) | Pore Volume (P/Po ≈ 1) |
| A | 16.7 m$^2$/g | 0.032 ml/g | 234 m$^2$/g | 0.415 ml/g |
| B | 14.3 | 0.031 | 227 | 0.449 |
| C | 330 | 0.193 | 270 | 0.362 |
| D*[2] | 195 | 0.128 | 209 | 0.693 |

*[1]P/Po = 0.976: Pore volume of pores having pore radius smaller than 600 Å
*[2]Zeodent 113 (Made by Huber Corp.)

TABLE 2

| Silica | Refractive Index | Liquid Absorption (ml/g) | Specific Gravity | Average Particle Size* (μm) | Abrasiveness (mg) |
|---|---|---|---|---|---|
| A | 1.435 | 1.01 | 2.142 | 0.2 | 7.5 |
| B | 1.440 | 1.05 | 2.188 | 0.3 | 6.8 |
| C | 1.461 | 1.11 | 2.135 | 0.3 | 10.5 |
| D | 1.445 | 0.98 | 2.128 | 0.02 | 5.1 |

*According to SEM method

TABLE 3

| | Example 1 | Example 2 | Comparative Example 1 | Comparative Example 2 |
|---|---|---|---|---|
| Silica A | 18% | | | |
| Silica B | | 18% | | |
| Silica C | | | 18% | |
| Silica D | | | | 18% |
| Silica thickening agent | 2.0 | 2.0 | 2.0 | 2.0 |
| 96% Glycerin | 17.9 | 18.9 | 22.9 | 19.9 |
| 70% Sorbitol | 35.8 | 37.7 | 45.8 | 39.7 |
| Polyethylene glycol 400 | 5.0 | 5.0 | 5.0 | 5.0 |
| Sodium carboxymethylcellulose | 1.2 | 1.2 | 1.2 | 1.2 |
| Sodium lauryl sulfate | 1.5 | 1.5 | 1.5 | 1.5 |
| Sodium saccharin | 0.1 | 0.1 | 0.1 | 0.1 |
| Flavor | 1.0 | 1.0 | 1.0 | 1.0 |
| Purified water | 17.5 | 14.6 | 2.5 | 11.6 |
| Total | 100.0 | 100.0 | 100.0 | 100.0 |
| Refractive index of toothpaste | 1.435 | 1.440 | 1.461 | 1.445 |

The properties of silica shown in Tables 1 and 2 were measured according to the following methods

Nitrogen adsorption

The adsorption isotherm for nitrogen is measured at the liquid nitrogen temperature (−196° C.).

The sample is outgassed under vacuum (1×10$^{-4}$ mmHg or below) at 105° C. for 5 hours or longer prior to adsorption.

(1) Specific surface area

The specific surface area per gram of anhydrous silica is calculated from the adsorption isotherm according to the BET method. It is assumed that the sectional area of a nitrogen molecule is 16.2 Å$^2$.

(2) Pore volume

The adsorption at a relative pressure of 0.967 (corresponding to a pore diameter of 600 Å) calculated from the adsorption isotherm is regarded as the pore volume. The relative pressure is the ratio of the vapor pressure at the time of measurement to the saturated vapor pressure

Water vapor adsorption

The adsorption isotherm for water vapor is measured at 25° C. according to the desiccator method. The samples should be dried at 105° C. for 5 hours or longer.

(1) Specific surface area

The specific surface area per gram of anhydrous silica is calculated from the adsorption isotherm according to the BET method. It is assumed that the sectional area of a water molecule is 12.5 Å$^2$.

(2) Pore volume

The adsorption at a relative pressure of 1.00 (saturated vapor pressure) calculated from the adsorption isotherm is regarded as the pore volume.

Refractive index

· Glycerin and water are mixed in varied ratios to prepare dispersing media having different refractive indexes. Each sample (15 g) is dispersed in 35 g of the respective dispersing media. Degassing and mixing are performed for 10 minutes by using a vacuum stirring grinder.

The refractive index and turbidity of each mixture are measured at 25° C., and refractive index-turbidity curves are drawn. The refractive index at which the turbidity is minimum is regarded as the refractive index of the sample tested.

The refractive index is measured with an Abbe refractometer and the turbidity is measured with a turbidimeter with integrating sphere. The turbidity is calculated from the transmittance of a 1 mm thick sample.

Liquid absorption

The sample is dried at 105° C. for 2 hours to remove water. 1.0 g of anhydrous sample is placed on a glass plate. 5 ml of 42.5% aqueous solution of glycerin is added little by little from a microburet, during which the sample and the liquid are uniformly mixed with a stainless steel spatula. Mixing is continued until the sample becomes granular and finally a putty-like lump which does not stick to the glass plate. The amount (ml) of the solution required for the sample to reach such a state is regarded as the liquid absorption.

Specific gravity (1) Calibration of pycnometer (i) Dry a 25 ml pycnometer at 105° C., and measure the weight ($W_p$).

(ii) Fill the pycnometer with distilled water which has been boiled and cooled and allow the pycnometer to stand in the balance room. Stopper the pycnometer and weigh it, recording the weight ($W_L$) to the nearest tenth of a milligram.

(iii) Immediately after weighing, put a thermometer in the pycnometer and measure the water temperature ($T_a$).

Calculate the volume ($V_4$) of the pycnometer at 4° C. from the following equation.

$$V_4 \text{ (ml)} = \frac{(W_L - W_P) \cdot \delta_a}{1 + \alpha(T_a - 4)}$$

where $\delta_a$: specific volume of water at $T_a$° C.

$\alpha$: coefficient of volume expansion of glass (0.000033)

(2) Measurement of specific gravity (i) Previously determine the content of free water (mf %) in the sample. Place about 1.0 g of sample in a pycnometer and measure the weight ($W_S$).

(ii) Add distilled water until the surface of the water is about 0.5 cm above the surface of the sample. Repeat several times the steps of evacuating and returning to normal pressure. Fill the pycnometer with distilled water and allow it to stand in the balance room. After the water has become clear, stopper the pycnometer. Measure the weight ($W_{S+L}$) and the temperature ($T_b$).

The weight (W) on dry basis of the sample:

$$W \text{ (g)} = \frac{W_S - W_P}{1 + 0.01 \times mf(\%)}$$

The volume ($V_b$) of the pycnometer at $T_b$° C.:

$$V_b(ml) = V_4 \cdot \{1 + \alpha(T_b - 4)\}$$

The specific gravity (S) of the sample:

$$S = \frac{W}{V_b - (W_{S+L} - W_P - W) \cdot \delta_b}$$

where $\delta_b$ is the specific volume of water at $T_b$° C.

Average particle diameter

The average particle diameter (model diameter) is measured by observation under a scanning electron microscope.

Abrasiveness (copper plate grinding method)

A copper plate with a smooth surface is ground 20,000 strokes under a load of 500 g by using a brushing-type grinder (inclined), and the loss of weight after grinding is regarded as abrasiveness. The grinding is carried out in a dispersion composed of 15 g of sample and 70 g of 60% aqueous solution of glycerin (containing 0.4% of sodium carboxymethylcellulose).

Four kinds of transparent toothpaste prepared according to the formulation shown in Table 3 were evaluated with respect to storage stability, feeling of use, and ropiness The results are shown in Tables 4 and 5.

TABLE 4

| | Storage Stability (Turbidity) | | | |
|---|---|---|---|---|
| | Immediately after preparation | After 1 month storage at room temperature | After 1 month storage at 40° C. | After 1 month storage at 50° C. |
| Example 1 | 0.11 | 0.11 | 0.12 | 0.12 |
| Example 2 | 0.10 | 0.11 | 0.11 | 0.12 |
| Comparative Example 1 | 0.09 | 0.10 | 0.11 | 0.11 |
| Comparative Example 2 | 0.12 | 0.15 | 0.28 | 0.35 |

Note:
Turbidity was measured with a turbidimeter with integrating sphere, and the sample thickness was 1 mm.

TABLE 5

| | Feeling of use | Ropiness |
|---|---|---|
| Example 1 | o | o |
| Example 2 | o | o |
| Comparative Example 1 | Δ | x |
| Comparative Example 2 | o | o |

Note:
Criterion for evaluation of feeling of use.
o: Good;
Δ: Fair;
x: Poor (evaluated by 10 expert panelists)
Criterion for evaluation of ropiness.
o: No;
Δ: Slight;
x: Severe EXAMPLES 3 to 6 and COMPARATIVE EXAMPLES 3 to 6

Four kinds of transparent toothpaste in which silica E (of this invention) and silica D (commercial product) having the properties shown in Table 6 are used as an abrasive where prepared according to the formulation shown in Table 7. Silica E was produced in the following manner.

In a 20-liter reaction vessel equipped with a 150-mm diameter turbin blade stirrer and baffles was placed 10 kg of aqueous solution of sodium silicate ($Na_2O.3.1 SiO_2$) containing 110 g/kg of $SiO_2$ and 15 g/kg of NaCl. While the reaction temperature was kept at 90° C., 10% sulfuric acid was added at a rate of 54 g/min for 76 minutes, so that the reaction system was adjusted to pH 10.0. Then, 10% sulfuric acid was added at a rate of 97 g/min for 14 minutes until the reaction system reached pH 7.2, which was followed by aging for 20 minutes. The precipitates were filtered and washed with water repeatedly, and finally dried in a drier at 110° C. and pulverized.

TABLE 6

| Property | Silica E | Silica D* |
| --- | --- | --- |
| Nitrogen adsorption | | |
| Specific surface area (BET method): m²/g | 36 | 195 |
| Pore volume: ml/g | 0.038 | 0.128 |
| Water vapor adsorption | | |
| Specific surface area (BET method): m²/g | 238 | 209 |
| Pore volume: ml/g | 0.458 | 0.693 |
| Specific surface area (CTAB method): m²/g | 22 | 45 |
| Difference between specific surface area (nitrogen adsorption) measured by BET method and CTAB method: m²/g | 14 | 150 |
| Refractive index | 1.440 | 1.445 |
| Liquid absorption: ml/g | 1.10 | 0.98 |
| Specific gravity | 2.119 | 2.128 |
| Average particle diameter: μm | 0.2 | 0.02 |
| Abrasiveness: mg | 6.7 | 5.1 |
| Turbidity | | |
| Immediately after mixing | 0.11 | 0.23 |
| After 5 days storage | 0.12 | 0.85 |

*Silica D is Zeodent 113 made by Huber Corp.

The specific surface area by CTAB method was measured in the following manner, and the other properties were measured as mentioned above.

Measurement of specific surface area by CTAB method

The specific surface area per gram of anhydrous silica is calculated from the amount of cetyl trimethylammonium bromide (CTAB) adsorbed (saturated) on the surface of sample silica in an aqueous solution. The sectional area of CTAB molecule is assumed to be 35 Å².

Weigh 1 g of sample containing a known amount of water into a 300-ml Erlenmeyer flask with ground stopper. Add 100 ml of 0.55% CTAB solution. Adjust the solution to pH 9.0 with N/10 NaOH solution, and stir the solution for 2 hours with a magnetic stirrer. Centrifuge the suspension, and transfer 10 ml of the supernatant liquid to a 300-ml Erlenmeyer flask for titration. Add 50 ml of deionized water, 25 ml of chloroform, and bromophenol blue indicator. Titrate with a solution of dioctyl sodium sulfosuccinate ("Aerosol OT") which has previously been standardized with a standard CTAB solution, until an end point is reached at which the chloroform layer becomes colorless and the water layer turns slightly purple. Record the amount ($V_2$ ml) of the titrant (Aerosol OT solution). Run a blank test using a sample which has not undergone the adsorption step and 10 ml of CTAB solution in the same manner as mentioned above. Record the amount ($V_1$ ml) of the titrant (Aerosol OT solution).

Calculate the surface area (S m²/g) per gram of the anhydrous sample from the following equation.

$$S = \frac{5.78 \times (V_1 - V_2) \times a}{X}$$

where
X: weight (g) of sample in terms of anhydride
a: amount (mg) of CTAB corresponding to 1 ml Aerosol solution.

TABLE 7

| Ingredient | I | II | III | IV |
| --- | --- | --- | --- | --- |
| Silica abrasive | 20% | 20% | 20% | 20% |
| 96% glycerin | 18.0 | 18.9 | 19.9 | 20.8 |
| 70% sorbitol | 35.7 | 37.7 | 39.7 | 41.7 |
| Polyethylene glycol 400 | 5.0 | 5.0 | 5.0 | 5.0 |
| Sodium carboxymethylcellulose | 1.2 | 1.2 | 1.2 | 1.2 |
| Sodium lauryl sulfate | 1.5 | 1.5 | 1.5 | 1.5 |
| Sodium saccharin | 0.1 | 0.1 | 0.1 | 0.1 |
| Flavor | 1.0 | 1.0 | 1.0 | 1.0 |
| Purified water | 17.5 | 14.6 | 11.6 | 8.7 |
| Total | 100.0% | 100.0% | 100.0% | 100.0% |
| Retractive index of toothpaste | 1.435 | 1.440 | 1.445 | 1.450 |

The transparent toothpaste was prepared by mixing glycerin, sorbitol, polyethylene glycol, and those ingredients soluble in them; dispersing sodium carboxymethylcellulose into the mixture; and finally adding silica, water, and sodium lauryl sulfate, followed by degassing and mixing with a vacuum mixing grinder.

Immediately after preparation, the toothpaste was filled into a laminate tube having an aluminum layer. The packed toothpaste was stored at room temperature or at 50° C. in a thermostat for 1 month. The clarity of the toothpaste was evaluated by measuring turbidity with a turbidimeter with integrating sphere. In measurement, the sample thickness was 1 mm and a filter of wavelength 594 nm was used.

Table 8 shows the results of evaluation of the toothpaste incorporated with silica E which conforms to this invention. Table 9 shows the results of evaluation of the toothpaste incorporated with silica D which is a commercial product for comparison.

TABLE 8

Turbidity of Toothpaste Incorporated with Silica E

| | Toothpaste | Immediately after preparation | After storage at room temperature | After storage at 50° C. |
| --- | --- | --- | --- | --- |
| Example 3 | I | 0.26 | 0.23 | 0.22 |
| Example 4 | II | 0.10 | 0.11 | 0.11 |
| Example 5 | III | 0.20 | 0.23 | 0.24 |
| Example 6 | IV | 0.53 | 0.55 | 0.58 |

TABLE 9

Turbidity of Toothpaste Incorporated with Silica D

| | Toothpaste | Immediately after preparation | After storage at room temperature | After storage at 50° C. |
| --- | --- | --- | --- | --- |
| Comparative Example 3 | I | 0.30 | 0.64 | 0.82 |
| Comparative Example 4 | II | 0.18 | 0.30 | 0.52 |
| Comparative Example 5 | III | 0.27 | 0.20 | 0.30 |
| Comparative Example 6 | IV | 0.58 | 0.30 | 0.18 |

It is noted from Tables 8 and 9 that the toothpaste incorporated with silica E according to the present invention keeps its transparency over a long period of storage even at a high temperature.

EXAMPLES 7 to 10

Four kinds of transparent toothpaste incorporated with silicate F to I having the properties shown in Table 10 were prepared according to the formulation shown in Table 11. The toothpaste samples were stored at room temperature, 40° C., or 50° C. for 1 month, and they were examined for turbidity immediately after preparation and after storage in the same manner as mentioned above. The results are shown in Table 12.

TABLE 10

| Property | Silicate F | Silicate G | Silicate H | Silicate I |
|---|---|---|---|---|
| Nitrogen adsorption | | | | |
| Specific surface area (BET method): m²/g | 31 | 47 | 38 | 53 |
| Pore volume: ml/g | 0.039 | 0.041 | 0.028 | 0.043 |
| Water vapor adsorption | | | | |
| Specific surface area (BET method): m²/g | 234 | 241 | 225 | 238 |
| Pore volume: ml/g | 0.421 | 0.445 | 0.410 | 0.450 |
| Specific surface area (CTAB method): m²/g | 15 | 19 | 23 | 42 |
| Difference between specific surface area (nitrogen adsorption) measured by BET method and CTAB method: m²/g | 16 | 28 | 15 | 11 |
| Refractive index | 1.437 | 1.441 | 1.436 | 1.442 |
| Liquid absorption: ml/g | 1.08 | 1.12 | 1.05 | 1.01 |
| Specific gravity | 2.185 | 2.176 | 2.188 | 2.181 |
| Average particle diameter: μm | 0.15 | 0.15 | 0.20 | 0.15 |
| Abrasiveness: mg | 7.2 | 5.1 | 6.8 | 5.0 |
| Metal content: | $Al_2O_3$ | $ZrO_2$ | $TiO_2$ | MgO |
| % by weight of $SiO_2$ | 0.5 | 0.5 | 0.5 | 0.5 |

TABLE 11

| Ingredient | Example 7 | Example 8 | Example 9 | Example 10 |
|---|---|---|---|---|
| Silicate F | 20% | | | |
| Silicate G | | 20% | | |
| Silicate H | | | 20% | |
| Silicate I | | | | 20% |
| Silica thickening agent | 2.0 | 2.0 | 2.0 | 2.0 |
| 96% Glycerin | 18.5 | 19.2 | 18.0 | 19.5 |
| 70% Sorbitol | 36.0 | 37.5 | 36.0 | 37.7 |
| Polyethylene glycol | 4.0 | 4.0 | 4.0 | 4.0 |
| Sodium carboxymethylcellulose | 1.2 | 1.2 | 1.2 | 1.2 |
| Sodium lauryl sulfate | 1.5 | 1.5 | 1.5 | 1.5 |
| Sodium saccharin | 0.1 | 0.1 | 0.1 | 0.1 |
| Flavor | 1.0 | 1.0 | 1.0 | 1.0 |
| Purified water | 15.7 | 13.5 | 16.2 | 13.0 |
| Total | 100.0% | 100.0% | 100.0% | 100.0% |
| Refractive index of toothpaste | 1.437 | 1.441 | 1.436 | 1.442 |

TABLE 12

| Toothpaste | Turbidity Immediately after preparation | After storage at room temperature | After storage at 40° C. | After storage at 50° C. |
|---|---|---|---|---|
| Example 7 | 0.21 | 0.22 | 0.24 | 0.24 |
| Example 8 | 0.14 | 0.15 | 0.16 | 0.18 |
| Example 9 | 0.06 | 0.06 | 0.08 | 0.08 |
| Example 10 | 0.04 | 0.04 | 0.05 | 0.05 |

It is noted from Table 12 that the transparent toothpaste of this invention keeps transparency without syneresis over a long period of storage even at a high temperature, and that it has good feeling during use and no tendency toward ropiness.

EXAMPLE 11

In a 200-liter reaction vessel equipped with a 350-mm diameter turbin blade stirrer and baffles was placed 105 kg of aqueous solution of sodium silicate ($Na_2O.3.1 SiO_2$) containing 100 g/kg of $SiO_2$ and 20 g/kg of NaCl. While the reaction temperature was kept at 87° C., 10% sulfuric acid was added at a rate of 0.38 kg/min for 102 minutes, so that the reaction system was adjusted to pH 10.0. Then, 10% sulfuric acid was added at a rate of 0.83 kg/min for 16 minutes until the reaction system reached pH 7.1, which was followed by aging for 15 minutes. The precipitates were filtered and washed with water repeatedly, and finally dried in a drier at 110° C. and pulverized.

The silica thus obtained had a proper degree of abrasiveness, good time-dependent stability, and other desirable properties for transparent toothpaste as shown below.

Specific surface area (BET method with nitrogen): 31 m²/g
Pore volume (with nitrogen): 0.042 ml/g
Specific surface area (BET method with water vapor): 230 m²/g
Pore volume (with water vapor): 0.418 ml/g
Specific surface area (CTAB method): 15 m²/g
Difference between specific surface area (BET method with nitrogen) and specific surface area (CTAB method): 16 m²/g
Liquid absorption: 1.10 ml/g
Average particle diameter: 0.2 μm
Abrasiveness (loss on abrasion): 6.5 mg
Refractive index: 1.437
Minimum turbidity: 0.26

Aqueous solutions of glycerin, sorbitol, and polyethylene glycol each containing 30% of this silica were examined for refractive index and change in turbidity after storage. The results are shown in Table 13.

TABLE 13

| Humectant | Turbidity Immediately after mixing | Turbidity After 100* day storage | Refractive index |
|---|---|---|---|
| Glycerin solution | 0.26 | 0.38 | 1.437 |
| Sorbitol solution | 0.13 | 0.13 | 1.437 |
| Polyethylene glycol solution | 0.11 | 0.13 | 1.437 |

*Turbidity measured after storage at 50° C. for 100 days.

Table 14 below shows the properties of synthetic amorphous precipitated silica used in the following Examples 12 to 21.

TABLE 14

| Silica | Nitrogen adsorption Specific surface area m²/g | Nitrogen adsorption Pore volume ml/g | Water vapor adsorption Specific surface area m²/g | Water vapor adsorption Pore volume ml/g |
|---|---|---|---|---|
| J | 11.2 | 0.021 | 215 | 0.407 |
| K | 34.2 | 0.040 | 238 | 0.452 |
| L | 48.6 | 0.058 | 241 | 0.396 |

EXAMPLE 12

| | |
|---|---|
| Silica J | 5.0% |
| Thickening silica | 3.0 |
| Polyethylene glycol 400 | 4.0 |
| 96% glycerin | 20.5 |
| 70% sorbitol | 45.3 |
| Sodium carboxymethylcellulose | 1.5 |

| -continued | |
|---|---|
| Tocopherol acetate | 0.05 |
| Sodium lauryl sulfate | 1.1 |
| Sodium saccharin | 0.1 |
| Flavor | 1.0 |
| Erythrosine (FD & C red No. 3) | 0.0005 |
| Purified water | Balance |
| Total | 100.0 |

EXAMPLE 13

| | |
|---|---|
| Silica J | 10.0% |
| Thickening silica | 3.0 |
| Polyethylene glycol 400 | 4.0 |
| 70% sorbitol | 65.0 |
| Sodium carboxymethylcellulose | 1.2 |
| Tranexamic acid | 0.05 |
| sodium lauryl sulfate | 1.2 |
| Sodium saccharin | 0.1 |
| Flavor | 1.0 |
| Acid red | 0.0005 |
| Purified water | Balance |
| Total | 100.0 |

EXAMPLE 14

| | |
|---|---|
| Silica J | 15.0% |
| Thickening silica | 2.5 |
| Polyethylene glycol 400 | 4.0 |
| 96% glycerin | 12.0 |
| 70% sorbitol | 46.2 |
| Sodium carboxymethylcellulose | 1.1 |
| ε-Aminocaproic acid | 0.01 |
| β-Glycyrrhetinic acid | 0.01 |
| Sodium lauryl sulfate | 1.2 |
| Sodium saccharin | 0.1 |
| Flavor | 1.0 |
| Tartrazine (FD & C yellow No. 5) | 0.001 |
| Purified water | Balance |
| Total | 100.0 |

EXAMPLE 15

| | |
|---|---|
| Silica J | 20.0% |
| Thickening silica | 2.0 |
| Polyethylene glycol 400 | 4.0 |
| 70% sorbitol | 62.5 |
| Sodium carboxymethylcellulose | 1.1 |
| Dipotassium glycyrrhizinate | 0.01 |
| Dextranase | 2000 u/g |
| Sodium lauryl sulfate | 1.5 |
| Sodium saccharin | 0.1 |
| Flavor | 1.0 |
| Brilliant blue FCF (FD & C blue No. 1) | 0.001 |
| Purified water | Balance |
| Total | 100.0 |

EXAMPLE 16

| | |
|---|---|
| Silica K | 9.0% |
| Thickening silica | 3.0 |
| Polyethylene glycol 400 | 5.0 |
| 70% sorbitol | 65.2 |
| Sodium carboxymethylcellulose | 1.2 |
| Sodium monofluorophosphate | 0.76 |
| Sodium lauryl sulfate | 1.2 |
| Sodium saccharin | 0.1 |
| Flavor | 1.0 |
| Tartrazine (FD & C yellow No. 5) | 0.001 |
| Brilliant blue | 0.0003 |

| -continued | |
|---|---|
| Purified water | Balance |
| Total | 100.0 |

EXAMPLE 17

| | |
|---|---|
| Silica K | 18.0% |
| Thickening silica | 2.0 |
| Polyethylene glycol 400 | 5.0 |
| 96% glycerin | 18.9 |
| 70% sorbitol | 43.0 |
| Sodium carboxymethylcellulose | 1.1 |
| Chlorhexidine gluconate | 0.01 |
| Sodium lauryl sulfate | 1.2 |
| Sodium saccharin | 0.1 |
| Flavor | 1.0 |
| Tartrazine (FD & C yellow No. 5) | 0.001 |
| Erythrosine (FD & C red No. 3) | 0.0005 |
| Purified water | Balance |
| Total | 100.0 |

EXAMPLE 18

| | |
|---|---|
| Silica K | 32.0% |
| Thickening silica | 2.0 |
| Polyethylene glycol 400 | 5.0 |
| 96% glycerin | 9.8 |
| 70% sorbitol | 38.5 |
| Sodium carboxymethylcellulose | 1.1 |
| Sodium monofluorophosphate | 0.76 |
| Sodium lauryl sulfate | 1.2 |
| Sodium saccharin | 0.1 |
| Flavor | 1.0 |
| Purified water | Balance |
| Total | 100.0 |

EXAMPLE 19

| | |
|---|---|
| Silica L | 15.0% |
| Thickening silica | 2.5 |
| Polyethylene glycol 400 | 4.0 |
| 96% glycerin | 10.5 |
| 70% sorbitol | 43.0 |
| Sodium carboxymethylcellulose | 1.2 |
| Sodium fluoride | 0.2 |
| Sodium lauryl sulfate | 1.5 |
| Sodium saccharin | 0.1 |
| Flavor | 1.0 |
| Purified water | Balance |
| Total | 100.0 |

EXAMPLE 20

| | |
|---|---|
| Silica L | 20.0% |
| Thickening silica | 2.0 |
| Polyethylene glycol 400 | 4.0 |
| 70% sorbitol | 63.8 |
| Sodium carboxymethylcellulose | 1.2 |
| Stannous fluoride | 0.4 |
| Sodium lauryl sulfate | 1.5 |
| Sodium saccharin | 0.1 |
| Flavor | 1.0 |
| Purified water | Balance |
| Total | 100.0 |

EXAMPLE 21

| | |
|---|---|
| Silica L | 25.0% |
| Thickening silica | 2.0 |
| Polyethylene glycol 400 | 4.0 |
| 96% glycerin | 5.0 |
| 70% sorbitol | 45.0 |
| Xanthane gum | 0.6 |
| Sodium monofluorophosphate | 0.76 |
| Sodium lauryl sulfate | 1.5 |
| Sodium saccharin | 0.1 |
| Flavor | 1.0 |
| Purified water | Balance |
| Total | 100.0 |

The compositions in Examples 12 to 21 were all stable.

What is claimed is:

1. A toothpaste composition, comprising:
an abrasive selected from the group consisting of amorphous silica, silicate and mixtures thereof having a specific surface area of 5 to 100 m$^2$/g as measured by the BET method with nitrogen adsorption and a specific surface area of 100 to 400 m$^2$/g as measured by the BET method with water vapor adsorption, said abrasive having a ratio of the specific surface area as measured by the BET method with water vapor absorption to the specific area as measured by the BET method with nitrogen adsorption of from 2 to 30.

2. The toothpaste composition as claimed in claim 1, wherein the pH is from 5 to 9.

3. The toothpaste composition as claimed in claim 1, wherein the abrasive has a pore volume of 0.01 to 0.15 mg/g as measured by the nitrogen adsorption method and a pore volume of 0.2 to 0.7 ml/g as measured by the water vapor adsorption method.

4. The toothpaste composition as claimed in claim 1, wherein the abrasive has a specific surface area of 5 to 60 m$^2$/g as measured by CTAB method.

5. The toothpaste composition as claimed in claim 1, wherein the abrasive has a specific surface area of 5 to 60 m$^2$/g as measured by the BET method with nitrogen adsorption and a specific surface area of 5 to 60 m$^2$/g as measured by the CTAB method, with the difference between the two values being less than 40 m$^2$/g.

6. The toothpaste composition as claimed in claim 1, wherein the silicate is aluminosilicate in which SiO$_2$ is combined with aluminium in an amount of less than 10% by weight based on the weight of SiO$_2$.

7. The toothpaste composition as claimed in claim 1, which is made transparent by incorporating the abrasive into a transparent toothpaste vehicle having substantially the same refractive index as the abrasive.

8. The toothpaste composition as claimed in claim 7, wherein the abrasive has a refractive index of 1.420 to 1.450.

9. The toothpaste composition as claimed in claim 1, which comprises 1-50% abrasive; 0-5% binder; 10-80% humectant; 0.1-5% surface active agent; a 0.01-5% sweetener; and a 0.1-5% flavoring; said percentages being by weight of said total toothpaste composition.

10. The toothpaste composition as claimed in claim 1, which comprises 5-35% abrasive; a 0.1-5% binder; a 30-60% humectant; a 0.5-2% surface active agent; a 0.05-2% sweetener; and a 0.5-2% flavoring; said component percentages being by weight of said total toothpaste composition.

11. The toothpaste composition as claimed in claim 1, wherein the average particle diameter of the abrasive is 0.01 to 1 μm as measured by the SEM method and 1 to 30 μm as measured by the sedimentation method.

12. The toothpaste composition as claimed in claim 1, wherein the average particle diameter of the abrasive is 0.05 to 0.5 μm as measured by the SEM method and 1-15 μm as measured by the sedimentation method.

13. The toothpaste composition as claimed in claim 1, wherein the abrasiveness of the abrasive is 1 to 50 mg as measured by the copper plate abrasion method.

14. The toothpaste composition as claimed in claim 13, wherein the abrasiveness of the abrasive is 1 to 20 mg.

15. The toothpaste composition according to claim 1 wherein the abrasive contains more than 70% by weight of SiO$_2$.

16. The toothpaste composition according to claim 6, wherein the amount of aluminum in the abrasive is less than 2% by weight based on SiO$_2$.

17. The toothpaste composition according to claim 1, wherein the silicate is zirconiumsilicate having less than 10% zirconium by weight based on the weight of SiO$_2$.

18. The toothpaste composition according to claim 1, wherein the abrasive contains less than 10% metal components based on the weight of SiO$_2$, said metal components being selected from the group consisting of sodium, potassium, lithium, calcium, magnesium and hafnium.

19. The toothpaste composition according to claim 1, wherein the abrasive has a water content less than 20% by weight at 25° C. and 70% relative humidity and has a loss upon ignition of less than 15%.

20. The toothpaste composition according to claim 8, wherein the refractive index is from 1.430 to 1.445.

21. The toothpaste composition according to claim 1, wherein the abrasive has a liquid absorption of 0.4 to 2.0 ml/g.

22. The toothpaste composition according to claim 5, wherein the abrasive has a specific surface area of 10 to 50 m$^2$/g as measured by the BET method with nitrogen adsorption and a specific surface area of 10 to 40 m$^2$/g as measured by the CTAB method, with the difference between the two values being less than 30 m$^2$/g.

23. The toothpaste composition according to claim 1, wherein the abrasive has a specific surface of 5 to 50 m$^2$/g as measured by nitrogen adsorption and a specific surface area of 150 to 300 m$^2$/g as measured by vapor adsorption, said ratio of said abrasive being 3 to 20.

24. The toothpaste composition according to claim 3, wherein the abrasive has a pore volume of 0.02 to 0.1 ml/g as measured by nitrogen absorption and a pore volume of 0.3 to 0.6 ml/g as measured by water vapor adsorption.

* * * * *